United States Patent

(12) United States Patent
Del Prete

(10) Patent No.: US 6,482,359 B2
(45) Date of Patent: Nov. 19, 2002

(54) PROCESS FOR THE STERILIZATION OF SEWER SYSTEMS AND CLOSED ROOMS IN GENERAL

(76) Inventor: Angelo Del Prete, Via Cassandro, 393, 47048-San Giovanni in Marignano (RN) (IT)

( * ) Notice: Subject to any disclaimer, the term of this patent is extended or adjusted under 35 U.S.C. 154(b) by 0 days.

(21) Appl. No.: 09/870,763

(22) Filed: May 31, 2001

(65) Prior Publication Data

US 2002/0031441 A1 Mar. 14, 2002

(30) Foreign Application Priority Data

Sep. 14, 2000 (IT) ........................................ MC00A0069

(51) Int. Cl.⁷ .............................. A61L 2/20; A61L 2/18
(52) U.S. Cl. ............................ 422/28; 422/24; 131/290
(58) Field of Search ....................... 422/28, 24; 131/290

(56) References Cited

U.S. PATENT DOCUMENTS 4,899,517 A * 2/1990 Shima et al. .................. 53/432
5,167,243 A * 12/1992 Cowan et al. ............... 131/290
5,213,759 A * 5/1993 Castberg et al. ............... 422/24
5,431,939 A * 7/1995 Cox et al. .................... 426/300
6,167,709 B1 * 1/2001 Caracciolo, Jr. et al. ........ 62/64

FOREIGN PATENT DOCUMENTS

| DE | 31 40 337 A1 | * | 4/1983 |
| DE | 43 16 572 A1 | * | 11/1994 |
| JP | 09165018 A | * | 6/1997 |

* cited by examiner

Primary Examiner—Robert J. Warden, Sr.
Assistant Examiner—Sean E. Conley
(74) Attorney, Agent, or Firm—Leonard Bloom; Robert M. Gamson

(57) ABSTRACT

The present invention relates to a process for the sterilization of sewer systems and other closed rooms consisting in the introduction and retention of a mixture of nitrogen and carbon dioxide—in gaseous, liquid or solid state—in a sealed environment.

7 Claims, No Drawings

PROCESS FOR THE STERILIZATION OF SEWER SYSTEMS AND CLOSED ROOMS IN GENERAL

The present patent application for industrial invention relates to a process for the sterilisation of sewer systems and closed rooms of any type.

It must be clearly stated that in this context the term "sterilisation" indicates not only the sterilisation process in the strict sense (that is the elimination of bacteria, microorganisms etc.), but also disinfestation, meaning the suppression of any kind of insects, reptiles (such as lizards and snakes), including small mammals (like rats and bats).

This type of sterilisation is normally performed in tunnels of sewer systems or in other closed rooms. The techniques used so far, however, present inconveniences and high risks.

As a matter of fact, sterilisation is currently performed by spraying powerful poison in liquid state or depositing "smoke" pills that sublimate in contact with air, releasing toxic gases.

It is obvious that the use of highly toxic substances causes serious problems, not only intoxication risks for the personnel in charge of their distribution, but also serious environmental damages when—once sterilisation has been completed—the sterilised rooms are open and the toxic substances disperse freely into the atmosphere.

The sterilisation process according to the invention has been devised in view of the above considerations, with the express purpose of overcoming the dangerous inconveniences of the previous technology.

The present invention is based on the sterilisation of closed rooms with a mixture of nitrogen and carbon dioxide in gaseous state, that is a compound of two non-toxic substances that are normally present in the atmosphere. More precisely, the substances used in the process are: nitrogen used for food production identified as E941 and carbon dioxide for food production identified as E290.

This mixture is capable of eliminating all the oxygen contained in a closed room and therefore cause the asphyxiation of all living beings.

This solution virtually eliminates health risks for the operators in charge of the sterilisation process, as well as air pollution risks, since the quantities of carbon dioxide and nitrogen dispersed in the air at the end of the process according to the present invention are not capable of significantly altering the composition of the surrounding air.

This description continues explaining the reason why the process according to the present invention necessarily makes use of a mixture of nitrogen and carbon dioxide, when it is known that each substance is capable of disinfesting a room according to the aforementioned procedure.

In fact, these two substances are considered as complementary, in view of the different specific weight once transformed into the gaseous state. In particular, nitrogen has a weight lower than air, while carbon dioxide has a higher weight.

For this reason, the nitrogen introduced in a room tends to rise upwards (that is towards the ceiling) while carbon dioxide tends to deposit downwards (that is towards the floor).

This explains how the combination of these two substances can completely saturate the volume of a closed room from the floor to the ceiling, thus ensuring the total elimination of all undesired living beings.

It can also be said that, once introduced in the room, the two substances form two layers one on top of the other (the lower layer of carbon dioxide and the upper layer of nitrogen) that are capable of completely saturating the air in the room and efficaciously sterilise all levels in the room.

It appears obvious that, a complete, efficacious disinfestation could not be obtained if only one of the two substances was used. When using carbon dioxide only, sterilisation would be limited to the bottom of the room, with no action on the ceiling, with the opposite situation when using nitrogen only.

As regards the practical execution of the sterilisation process according to the present invention, it must be said that the mixture of the two substances must be introduced in a previously sealed room (in order to avoid leaks and dispersions outside) and maintained there for at least twelve hours.

In particular, during the sterilisation of sewer systems, the process is performed in consecutive sections, after placing two sealing screens (made for instance of suitable nylon sheets) at the end of each section to be disinfested.

To this end, in the presence of ramifications of the sewer system, it is advisable to isolate them at the convergence point and intervene in each ramification separately.

As regards the distribution mode of the substances inside the room to be treated, it must be said that the two substances are preferably introduced in the rooms directly in gaseous state, stored in separate tanks that can be for instance installed on board of suitable vehicles.

The same result can also be obtained by introducing nitrogen in liquid state and carbon dioxide either in liquid or solid state. Regardless of their original state, when they get in contact with air inside the room to be disinfested, these substances sublimate and therefore change into gaseous state.

It must also be said that nitrogen in liquid and gaseous state is maintained at a temperature of about $-200°$ C., while carbon dioxide in liquid and gaseous state is maintained at a temperature of about $-80°$ C. A temperature much below zero is obtained during the sublimation process of carbon dioxide, when it changes from solid to gaseous state.

In this perspective it can be easily understood that a room disinfested with the process according to the present invention is characterised by a drastic reduction in temperature, both when the two substances are introduced in gaseous state and when they are introduced in liquid and solid state and then sublimated.

The drastic reduction in temperature produced inside the room gives an additional, important contribution to the outcome of the process according to the present invention, since it kills larvae and eggs of insects or other parasites that—until they remain in this state—would not be affected by the "asphyxiation" effect caused by the air saturation created by the mixture of nitrogen and carbon dioxide.

In view of the above, it can be finally stated that the combination of asphyxiation and hypothermia caused by the introduction of the two aforementioned substances in the room to be disinfested ensures the total sterilisation of the room, which is also maintained for a certain period of time.

What is claimed is:

1. A process for the sterilisation of sewer systems and closed rooms of any type, characterised by the introduction and retention of a mixture of nitrogen and carbon dioxide at a temperature of $-80°$ C. or colder in a sealed environment.

2. A process for the sterilisation of sewer systems and closed rooms of any type according to claim 1, characterised by the fact that nitrogen is used in gaseous or liquid state.

3. A process for the sterilisation of sewer systems and closed rooms of any type according to claim 1, characterised by the fact that carbon dioxide is used in gaseous, liquid or solid state.

4. The process of claim 1, wherein a lower layer of gaseous carbon dioxide and an upper layer of gaseous nitrogen are formed within the sewer systems and closed rooms.

5. The process of claim 1, wherein the mixture of nitrogen and carbon dioxide is maintained in the sealed environment for at least twelve hours.

6. A process for the sterilization of a sealed environment of sewer systems and closed rooms of any type comprising the steps of:

provuding liquid or gaseous nitrogen at a temperature of approximately −200° C.;

providing solid liquid or gaseous carbon dioxide at a temperature of approximately −80° C.;

introducing the nitrogen into the sealed environment wherein the gaseous nitrogen tends to rise toward a ceiling of the sealed environment;

introducing the carbon dioxide into the sealed environment wherein the gaseous carbon dioxide tends to collect towards a floor of the sealed environment;

thereby forming a top gaseous layer and a bottom gaseous layer maintained for at least twelve hours wherein the sealed environment is sterilized by asphyxiation and hypothermia.

7. The process of claim 6, wherein the temperature of at least −80° C. is maintained in the sealed environment.

* * * * *